US00PP34762P2

(12) United States Plant Patent
Hartman

(10) Patent No.: US PP34,762 P2
(45) Date of Patent: Nov. 22, 2022

(54) ***CALADIUM* PLANT NAMED 'RIB WT OF13-530'**

(50) Latin Name: ***Caladium* X *hortulanum***
Varietal Denomination: RIB WT OF13-530

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/741,103

(22) Filed: May 10, 2022

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — C. Anne Whealy

(57) ABSTRACT

A new and distinct cultivar of *Caladium* plant named 'RIB WT OF13-530', characterized by its compact and upright to mounding plant habit; dense, leafy and bushy appearance; vigorous growth habit and rapid growth rate; narrow lance-type leaves with long tapering apices that are greyish yellow green in color with dark green-colored margins; and petioles that are green in color.

4 Drawing Sheets

Figure 1:
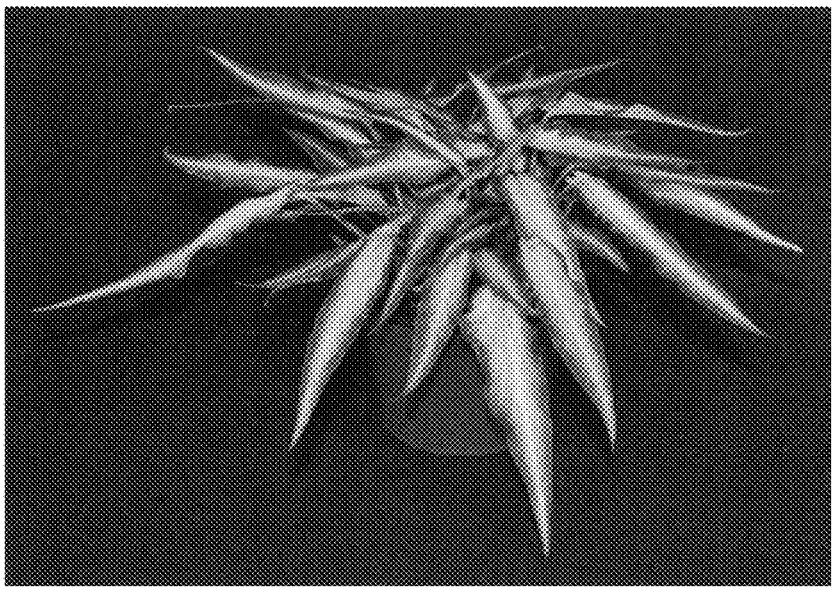

Botanical designation: *Caladium* X *hortulanum.*
Cultivar denomination: 'RIB WT OF13-530'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum,* commercially referred to as a lance leaf-type *Caladium* and hereinafter referred to by the name 'RIB WT OF13-530'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'RS-03-03', disclosed in U.S. Plant Pat. No. 26,265, as the female, or seed, parent with *Caladium* X *hortulanum* 'White Delight', disclosed in U.S. Plant Pat. No. 21,216, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RIB WT OF13-530'. These characteristics in combination distinguish 'RIB WT OF13-530' as a new and distinct *Caladium* plant:

1. Compact and upright to mounding plant habit; dense, leafy and bushy appearance.
2. Vigorous growth habit and rapid growth rate.
3. Narrow lance-type leaves with long tapering apices that are greyish yellow green in color with dark green-colored margins.
4. Petioles that are green in color.

Plants of the new *Caladium* differ primarily from plants of the female parent, 'RS-03-03', in the following characteristics:

1. Plants of the new *Caladium* are more compact than plants of 'RS-03-03'.
2. Leaves of plants of the new *Caladium* are narrower than leaves of plants of 'RS-03-03'.
3. Leaves of plants of the new *Caladium* are greyish yellow green in color with dark green-colored margins whereas leaves of plants of 'RS-03-03' are pearlescent white to greenish white in color with dark green-colored margins and white to greenish white-colored venation.

Plants of the new *Caladium* differ primarily from plants of the male parent, 'White Delight', in the following characteristics:

1. Plants of the new *Caladium* are more compact than plants of 'White Delight'.
2. Leaves of plants of the new *Caladium* are narrower than leaves of plants of 'White Delight'.
3. Leaves of plants of the new *Caladium* are greyish yellow green in color with dark green-colored margins whereas leaves of plants of 'White Delight' are white to grey-green in color with white-colored main veins and dark green-colored borders.
4. Leaf petioles of plants of the new *Caladium* are green in color whereas leaf petioles of plants of 'White Delight' are green in color, tinged with light brown and with darker green-colored stippling, streaks and tessellations.

Plants of the new *Caladium* can be compared to plants of *Caladium* X *hortulanum* 'White Dynasty', disclosed in U.S. Plant Pat. No. 22,240. In side-by-side comparisons, plants of the new *Caladium* differ primarily from plants of 'White Dynasty' in the following characteristics:

1. Plants of the new *Caladium* are more compact than plants of 'White Dynasty'.
2. Leaves of plants of the new *Caladium* are narrower than leaves of plants of 'White Dynasty'.
3. Leaves of plants of the new *Caladium* are greyish yellow green in color with dark green-colored margins whereas leaves of plants of 'White Dynasty' are white and greyed green in color with few random red purple-colored spots, dark green-colored margins and greyed green-colored venation.
4. Leaf petioles of plants of the new *Caladium* are green in color whereas leaf petioles of plants of 'White Dynasty' are green in color tinged with green and purplish brown.

Plants of the new *Caladium* can also compared to plants of *Caladium* X *hortulanum* 'White Wonder', disclosed in U.S. Plant Pat. No. 21,044. In side-by-side comparisons, plants of the new *Caladium* differ primarily from plants of 'White Wonder' in the following characteristics:

1. Plants of the new *Caladium* are more compact than plants of 'White Wonder'.
2. Leaves of plants of the new *Caladium* are narrower than leaves of plants of 'White Wonder'.
3. Leaves of plants of the new *Caladium* are greyish yellow green in color with dark green-colored margins whereas leaves of plants of 'White Wonder' are white to grey-green in color with light pink to white-colored venation and dark green-colored borders.
4. Leaf petioles of plants of the new *Caladium* are green in color whereas leaf petioles of plants of 'White Wonder' are tannish pink in color with greenish brown-colored stripes.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'RIB WT OF13-530' grown in a container that has not had its tuber de-eyed prior to planting.

Figure 2:
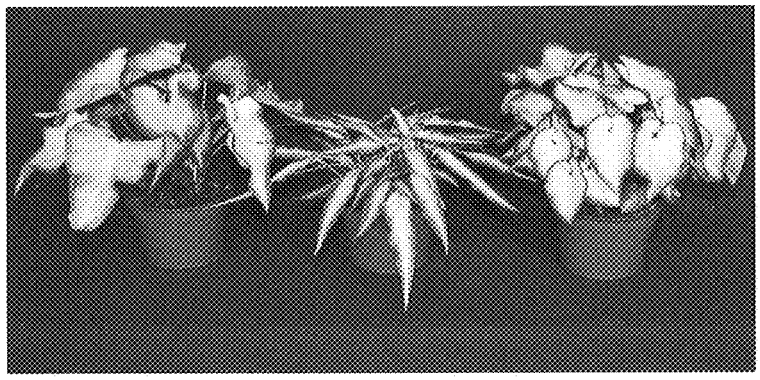

The photograph at the top of the second sheet (FIG. 2) is side perspective view of typical plants of the female parent, 'RS-03-03' (left), 'RIB WT OF13-530' (center) and the male parent, 'White Delight' (right).

Figure 3:
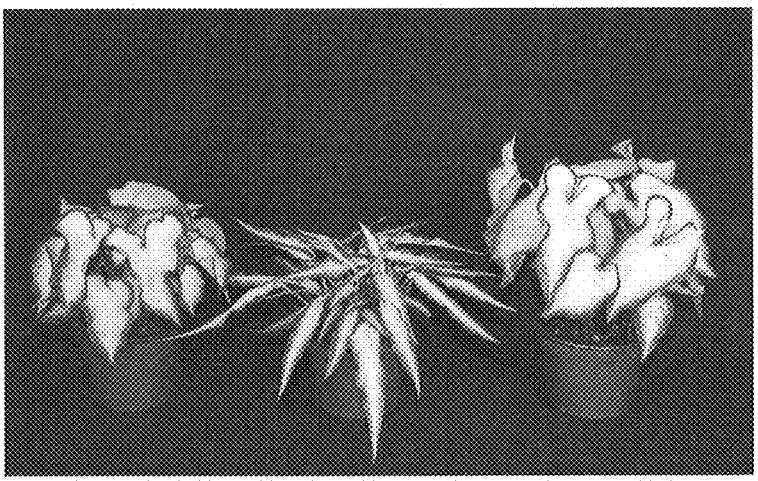

The photograph at the bottom of the second sheet (FIG. 3) is side perspective view of typical plants of 'White Dynasty' (left), 'RIB WT OF13-530' (center) and 'White Wonder' (right).

Figure 4:
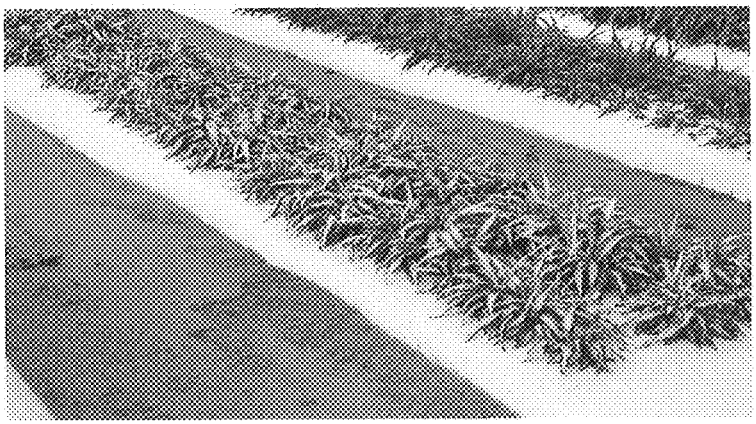

The photograph at the top of the third sheet (FIG. 4) is a side perspective view of typical plants of 'RIB WT OF13-530' grown in an open production field.

Figure 5:
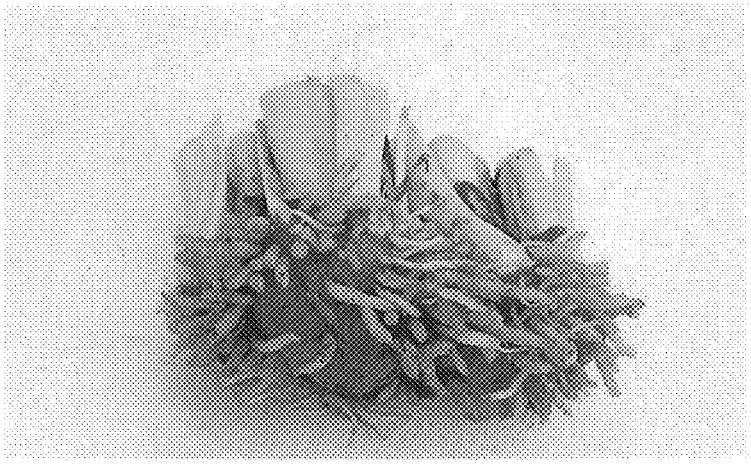

The photograph at the bottom of the third sheet (FIG. 5) is a close-up view of typical freshly-harvested tubers with roots and leaf petioles of 'RIB WT OF13530'.

Figure 6:
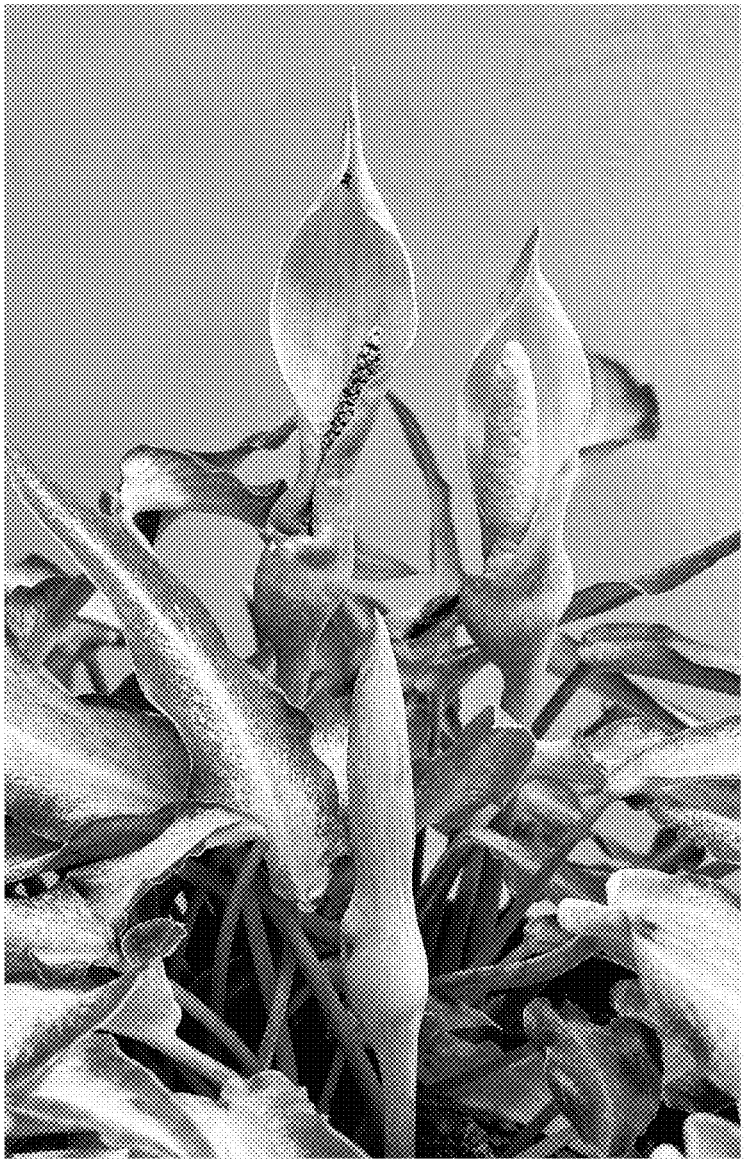

The photograph on the fourth sheet (FIG. 6) is a close-up view of typical inflorescences of 'RIB WT OF13-530'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were eight weeks old and plants grown in the outdoor nursery were 5.5 months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'RIB WT OF13-530'.

Parentage:

*Female, or seed, parent.*—*Caladium* X *hortulanum* 'RS-03-03' disclosed in U.S. Plant Pat. No. 26,265.

*Male, or pollen, parent.*—*Caladium* X *hortulanum* 'White Delight', disclosed in U.S. Plant Pat. No. 21,216.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments are elliptic to irregular in shape. Height: About 2.2 cm to 2.3 cm. Diameter: About 5.3 cm to 6.5 cm.

Segment height: About 1.6 cm to 2.2 cm. Segment diameter: About 1.7 cm to 2.3 cm. Axillary bud shape: Roughly triangular. Axillary bud height: About 4.5 mm. Axillary bud width: About 4 mm. Texture: Thick, starchy; somewhat brittle. Color: Periderm, freshly-harvested: Close to N199B to N199D. Periderm, dried: Close to 200A to 200B. Epidermis: Close to 179B. Cortical tissue: Close to 10C and 10D. Axillary buds: Close to 49D and 38D. Root description: Thick, fleshy contractile roots with numerous fine lateral branches; color, close to NN155D, actual color of the roots is dependent on substrate composition, water quality, fertilizer type and formulation, substrate temperature and physiological age of roots. Rooting habit: Dense.

Plant description:

*Plant type.*—Herbaceous perennial; suitable as a potted plant in containers 10-cm to 25-cm and suitable as a landscape plant in shaded areas.

*Plant and growth habit.*—Compact and upright to mounding plant habit; dense, leafy and bushy appearance; vigorous growth habit and rapid growth rate; potted plants finish in saleable form in about eight weeks after planting tubers; leaf petioles and leaves arise from one or more growing points on tubers; leaf petioles initially upright and arching outwardly with development; mature leaves are horizontal to arching downward.

*Plant height, from soil level to top of foliar plane, shade house-grown potted plants.*—About 13 cm to 18 cm.

*Plant height, from soil level to top of floral plane, shade house-grown potted plants.*—About 15.2 cm to 17.9 cm.

*Plant diameter, shade house-grown potted plants.*—About 35 cm to 39 cm.

*Number of shoots per plant, shade house-grown potted plants, tubers not de-eyed.*—About 12 to 15 develop per #1 tuber.

*Cataphylls, shade house-grown potted plants.*—Length: About 4.5 cm to 5.2 cm. Width: About 6 mm. Shape: Lanceolate, strap-shaped. Apex: Acuminate. Base: Sheathing the stem. Texture and luster, outer and inner surfaces: Smooth, glabrous; semi-glossy. Color, outer surface: Close to 147C and 147D; towards the apex, close to 147B; can also be close to 147C tinged with close to 182D and stippled and streaked with close to 200C; color becoming closer to 200C with subsequent development. Color, inner surface: Close to 157D and 195C with colors and color patterns from outer surface visible.

Leaf description:

*Arrangement and type.*—Alternate; simple; narrow lance-type.

*Length, shade house-grown potted plants.*—About 10 cm to 21 cm.

*Width, shade house-grown potted plants.*—About 2.9 cm to 6.4 cm; when flattened, about 3 cm to 6.5 cm.

*Shape.*—Narrowly lanceolate; mature leaves adjacent to the inflorescence can be more ovate in shape.

*Apex.*—Long-tapered acuminate to acute and apiculate.

*Base.*—Sagittate, acute, cuneate and involute; basal lobes much reduced and variably folded forward and upwardly.

*Margin.*—Entire; very wavy with broad undulations.

*Texture and luster, upper surface.*—Smooth, glabrous; relatively thick and leathery; slightly glossy.

*Texture and luster, lower surface.*—Smooth, glabrous; slightly glaucous; dull sheen.

*Venation pattern.*—Pinnate and palmate.

*Color, shade house-grown potted plants.*—When developing, upper surface: Center: Close to 191B; towards the margins, close to 191B with flecks, close to 147A; towards the base, close to 147C and 147C to 147D, variably and faintly tinged with close to N187A. Margins: Close to 147A variably and faintly tinged with close to N186C; occasionally with flecks, close to 191A and 147C. Midvein: Close to 194B and 194B to 194C, can be streaked with close to 147B and 147C. Lateral venation: Close to 147B, 147C and 191B. When developing, lower surface: Center: Close to 191A to 191B and 147B; towards the base, close to 147C. Margins: Close to 191A or close to 191A variably and faintly tinged with close to N186C or 189A. Midvein: Close to 148C, 147C and 147D; proximally, can be tinged with close to 199A. Lateral venation: Close to 147A and 147B. Fully expanded leaves adjacent to the inflorescences, upper surface: Center: A suffusion of close to 191B, 191C, 194B, 147A and 148B; towards the base, close to 147C and 147C to 147D, variably and faintly tinged with close to N187A. Margins: Close to 147A; occasionally with flecks, close to 191A and 147C. Midvein and lateral venation: Close to 191B, 191C, 194B, 147A and 148B. Fully developed leaves adjacent to the inflorescences, lower surface: Center: Close to 147A, 147B and 157A; towards the base, close to 147C. Margins: Close to 191A or close to 191A variably and faintly tinged with close to 189A. Midvein: Close to 148C, 147C and 147D; proximally, can be tinged with close to 199A. Lateral venation: Close to 147A and 147B; areas surrounding the venation, close to 147C.

*Petioles.*—Aspect: Initially upright and straight and arching outwardly with development; flexible. Length, shade house-grown potted plants: About 7 cm to 12 cm. Diameter, distally, shade house-grown potted plants: About 3 mm. Diameter, proximally, shade house-grown potted plants: About 5 mm. Texture and luster: Smooth, glabrous; slightly glaucous. Color, shade house-grown potted plants: Close to 147A to 147B; with stippling, streaks and tessellations of close to N200A with subsequent development. Wing length, shade house-grown potted plants: About 3 cm to 4.5 cm. Wing diameter, shade house-grown potted plants: About 8 mm. Texture and luster, inner and outer surfaces: Smooth, glabrous; slightly glossy. Wing color, shade house-grown potted plants: Inner surface: Close to 157D and 195D; colors and patterns on the outer surface are visible on the inner surface. Outer surface: Close to 147C and 147D or close to 147C tinged with close to 182D and stippled, streaked and tessellated with close to 200B.

Inflorescence description:

*Inflorescence arrangement.*—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance.*—Night-fragrant; jasmine-like with camphor note.

*Natural flowering season and flower longevity.*—Plants of the new *Caladium* typically flower during the spring and summer in central Florida; flowers develop about ten weeks after growth commences; inflorescences last about three days before fading; inflorescences persistent.

*Spathe.*—Length, overall: About 7 cm. Length, distal open portion: About 5 cm. Length, proximal closed portion: About 2 cm. Width, distal open portion: About 2 cm. Depth, distal open portion: About 1.5 cm. Width, at constriction: About 1.1 cm. Width, proximal closed portion: About 1.5 cm. Shape, open portion: Narrowly elliptic. Apex: Acuminate. Base: Acute. Margin: Entire. Texture and luster, front surface: Smooth, glabrous; dull sheen. Texture and luster, rear surface: Smooth, glabrous; dull sheen; proximally, slightly glaucous. Color, front surface: Distal open portion: Close to 148D and 145D; with subsequent development, distally becoming closer to N200A. Proximal closed portion: Close to 148D and 147D; color does not change with subsequent development. Color, rear surface: Distal open portion: Close to 147D tinged with close to 146C; color does not change with subsequent development. Proximal closed portion: Close to 147C with streaks, close to 147B; color does not change with subsequent development.

*Spadix.*—Length, overall: About 5 cm. Length, male flower zone: About 2.9 cm. Length, sterile zone: About 1 cm. Length, female flower zone: About 1.1 cm. Diameter, male flower zone: About 7 mm. Diameter, sterile flower zone: About 5 mm. Diameter, female flower zone: About 5.5 mm. Shape: Columnar, spindle-shaped. Apex: Acute. Base: Obtuse. Aspect: Upright. Color, mature, male zone: Close to 158B tinged with close to 145C. Color, mature, sterile zone: Close to N155D. Color, mature, female zone: Close to 158D. Male flowers: Quantity per spadix: About 80. Shape: Obovate. Height: About 2.5 mm. Diameter: About 2.5 mm. Pollen amount: Sparse. Pollen color: Close to 11C and 11D. Female flowers: Quantity per spadix: About 72. Shape: Obovate. Height: About 2 mm. Diameter: About 1.5 mm. Stigma color: Close to 158D. Ovary color: Close to 159C faintly tinged with close to N170D.

*Scapes.*—Length: About 8.2 cm. Diameter: About 3 mm. Strength: Sturdy; flexible. Aspect: Mostly erect, straight. Texture and luster: Smooth, glabrous; dull sheen; slightly glaucous. Color: Close to 147C tinged with close to 137C.

*Seeds and fruits.*—To date, seed and fruit development have not been observed on plants of the new *Caladium.*

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RIB WT OF13-530' as illustrated and described.

* * * * *